(12) United States Patent
Lin et al.

(10) Patent No.: US 10,441,615 B2
(45) Date of Patent: Oct. 15, 2019

(54) METHOD FOR PREPARING FRESH CHLORELLA DRINK AND USE OF THE FRESH CHLORELLA DRINK

(71) Applicants: Ting-Jung Lin, Tainan (TW); Mei-Hua Huang, Taichung (TW)

(72) Inventors: Ting-Jung Lin, Tainan (TW); Mei-Hua Huang, Taichung (TW)

( * ) Notice: Subject to any disclaimer, the term of this patent is extended or adjusted under 35 U.S.C. 154(b) by 269 days.

(21) Appl. No.: 15/598,306

(22) Filed: May 17, 2017

(65) Prior Publication Data

US 2018/0333445 A1    Nov. 22, 2018

(51) Int. Cl.
| | | |
|---|---|---|
| A23L 29/00 | (2016.01) | |
| A61K 36/05 | (2006.01) | |
| C12N 1/12 | (2006.01) | |
| A61K 9/00 | (2006.01) | |
| A23L 2/52 | (2006.01) | |
| A23L 33/00 | (2016.01) | |
| A23L 33/105 | (2016.01) | |
| A23L 17/60 | (2016.01) | |

(52) U.S. Cl.
CPC .............. *A61K 36/05* (2013.01); *A23L 2/52* (2013.01); *A23L 17/60* (2016.08); *A23L 33/105* (2016.08); *A23L 33/30* (2016.08); *A61K 9/0095* (2013.01); *C12N 1/12* (2013.01); *A23V 2002/00* (2013.01)

(58) Field of Classification Search
CPC .................................................... A23L 29/065
See application file for complete search history.

(56) References Cited

U.S. PATENT DOCUMENTS

2010/0297295 A1* 11/2010 Brooks .................. A21D 2/165
426/61

* cited by examiner

*Primary Examiner* — Rosanne Kosson
(74) *Attorney, Agent, or Firm* — Pai Patent & Trademark Law Firm; Chao-Chang David Pai

(57) ABSTRACT

Provided is a method for preparing a fresh *Chlorella* drink by sterile culturing and freezing and then rapidly raising the temperature.

5 Claims, 3 Drawing Sheets

METHOD FOR PREPARING FRESH CHLORELLA DRINK AND USE OF THE FRESH CHLORELLA DRINK

BACKGROUND OF THE INVENTION

1. Field of the Invention

The present invention relates to a method, especially a method for preparing a fresh *Chlorella* drink by sterile culturing. The present invention also relates to the fresh *Chlorella* drink obtained by the method, particularly the fresh *Chlorella* drink containing *Chlorella* cells with no variation. The present invention further relates to a treatment with the fresh *Chlorella* drink, particularly, to anti-cancer treatment.

2. Description of the Prior Arts

*Chlorella* is plankton. When concentration of the *Chlorella* population is excessive, the *Chlorella* cells undergo autolysis to maintain the excellent survival and breeding environment for the *Chlorella* population. However, the autolytic *Chlorella* cells will produce harmful substances and also odor. Since the *Chlorella* is an extremely nutritious natural substance for other species, the *Chlorella* often becomes the host for other species in the natural environments. When the *Chlorella* cells are parasitized, they will produce unpredictable cell variation. In addition, the *Chlorella* can effectively adsorb heavy metals, pesticides, chemical toxins, polychlorinated binocene, dioxin, radiation and other toxins. As toxins accumulate, the *Chlorella* cells themselves will mutate.

According to studies, the planktonic algae cannot live and reproduce in rapid streams. As shown in FIG. 3, the conventional culturing method of the *Chlorella* relies on strong water flow stirring, fermentation culture and the open pond culture (the air culture) to keep the *Chlorella* cells suspending, and as long as the water flow is calm, the *Chlorella* cells will precipitate and die. Thus, the *Chlorella* cells of the commercial *Chlorella* products have undergone variations and are not original. In addition, any of the following conditions such as heat treatment at a temperature higher than 50° C., drying process (spray drying or freeze-drying), low temperature disruption, storage at higher than 0° C. over 6 hours, and standing still over 2 hours will make the *Chlorella* cells precipitated or induce variations of the *Chlorella* cells. Furthermore, the quantitative limits for heavy metal levels in *Chlorella* products as regulated by Chinese National Standards (CNS) in Taiwan has been changed from less than 5 ppm to less than 20 ppm. Thus, the *Chlorella* cells obtained from the conventional *Chlorella* culturing method have varied and been contaminated with environmental toxins.

SUMMARY OF THE INVENTION

In view of that the incubation time of the conventional *Chlorella* culture is too long, the heating and cell wall disruption cause *Chlorella* cells to vary and degenerate and contain environmental toxins, and the variant *Chlorella* cells will die once they precipitate, the object of the present invention is to provide a method for preparing a fresh *Chlorella* drink, by sterile culturing, freezing and then rapid heating to shorten the period of cultivation without causing *Chlorella* cells variations and keep the heavy metal content low.

To achieve the above object, the present invention provides a method for preparing a fresh *Chlorella* drink, comprising the steps of:

sterile culturing and stirring *Chlorella* for not longer than 3 days, and when the concentration of the *Chlorella* is over five ten thousandths, harvesting the culture of *Chlorella* within 6 hours;

rapidly cooling the harvested culture of *Chlorella* to lower than 1° C. but not frozen, then centrifuging the cooled culture of *Chlorella*, and adding sterile water to obtain a *Chlorella* suspension, wherein the concentration of the *Chlorella* is from 2.5 mg/ml to 12.5 mg/ml; and freezing the *Chlorella* suspension to be completely frozen below 0° C. and stand still from 12 hours to 24 hours and then increasing the temperature to the range from 40° C. to 50° C. within 10 minutes to obtain the fresh *Chlorella* drink.

Preferably, during the sterile culturing of the *Chlorella*, the speed of stirring is from 3 m/min to 20 m/min.

Preferably, in the step of freezing the *Chlorella* suspension to be completely frozen below 0° C. and stand still from 12 hours to 24 hours and then increasing the temperature to the range from 40° C. to 50° C. within 10 minutes to obtain the fresh *Chlorella* drink, the temperature may be raised by microwaves or infrared rays.

Preferably, in the step of freezing the *Chlorella* suspension to be completely frozen below 0° C. and stand still from 12 hours to 24 hours and then increasing the temperature to the range from 40° C. to 50° C. within 10 minutes to obtain the fresh *Chlorella* drink, the frozen temperature ranges from −1° C. to −21° C.

Preferably, in the step of freezing the *Chlorella* suspension to be completely frozen below 0° C. and stand still from 12 hours to 24 hours and then increasing the temperature to the range from 40° C. to 50° C. within 10 minutes to obtain the fresh *Chlorella* drink, the period of raising the temperature is from 3 minutes to 10 minutes.

The present invention further provides a fresh *Chlorella* drink obtained by the method as described above, which contains the *Chlorella* that preserves the effect of making the organisms healthy. Comparing the conventional *Chlorella* products with the fresh *Chlorella* drink of the present invention, significant differences are as follows: 1. The conventional *Chlorella* products have bad smell, while the fresh *Chlorella* drink of the present invention tastes good. 2. The fresh *Chlorella* drink can be absorbed completely by the human body without requiring the processing of cell wall disruption, while the conventional *Chlorella* products cannot be digested by the human body unless processed with cell wall disruption. 3. The content of *Chlorella* growth factor (CGF) of the fresh *Chlorella* drink obtained by the method according to the present invention is generally twice higher than that of the conventional *Chlorella* products. 4. The function of chlorophyll is preserved in the fresh *Chlorella* drink; however, the function of chlorophyll of the conventional *Chlorella* products is reduced during the heating process. 5. The present invention further provides a method for treating cancer comprising a step of administering to a subject a therapeutically effective amount of the fresh *Chlorella* drink.

According to the present invention, the term "treating cancer" as used herein, refers to treating, relieving or inhibiting cancer.

Preferably, the therapeutically effective amount of the fresh *Chlorella* drink is from 10 mg/kg to 200 mg/kg based on solid *Chlorella* contained in the fresh *Chlorella* drink.

According to the present invention, the term "therapeutically effective amount" as used herein, refers to a dosage to alleviate or inhibit progress of cancer. According to the present invention, the therapeutically effective amount is the amount effective for inhibiting or stopping growth of breast tumor, or even inducing death of breast tumor, and is determined by administering the anticancer pharmaceutical composition comprising the fresh *Chlorella* drink in a specific amount, and measuring the tumor volume in a specific period.

Preferably, the formulation of the anticancer pharmaceutical composition includes, but is not limited to, liquid.

The fresh *Chlorella* drink prepared by the method of the present invention without undergoing fermentation or outdoor culture not only shortens the culturing time, but also reduces the amount of heavy metal contained in the fresh *Chlorella* drink. In addition, with a low flow rate, the method according to the present invention does not cause *Chlorella* cells precipitation or variation. The method according to the present invention does not process cell wall disruption, spray drying with high heat or freeze-drying, so that the *Chlorella* cells will not incur variants, resulting in that the fresh *Chlorella* drink obtained by the method not only contains higher *Chlorella* growth factor and chlorophyll, but also has the anticancer effect.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
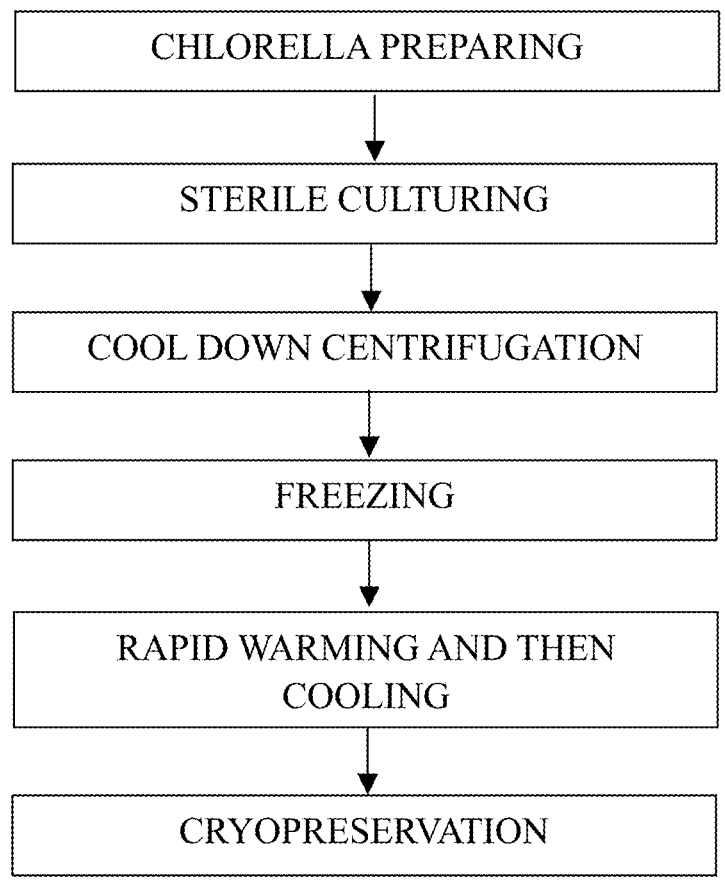
FIG. 1 is a flow chart of a method for preparing a fresh *Chlorella* drink of the present invention.

Before the present invention is described in greater detail with reference to the accompanying examples, it should be noted herein that like elements are denoted by the same reference numerals throughout the present invention.

PREPARATION EXAMPLE 1

Preparation of the Fresh *Chlorella* Drink

Referring to FIG. 1, the method for preparing the fresh *Chlorella* drink of the present invention comprises the steps of: (1) preparing *Chlorella*; (2) sterile culturing the *Chlorella* to obtain a mixture solution, wherein the carbon source needed by the *Chlorella* is filtered sterile air, the stirring speed is not faster than 20 meters per minute, and the culture period is not longer than 3 days. The culture time cannot be over 6 hours when the concentration of the mixture solution (based on the solid *Chlorella* in the mixture solution) reaches five ten thousandths, otherwise the *Chlorella* cells will start autolysis; (3) rapidly cooling down the mixture solution to below 1° C. (not frozen) and removing the medium by sterile centrifugation, after washing with sterile water at same temperature, starting sterile centrifugation again, and quantifying the *Chlorella* cells with sterile water to 5% to obtain a *Chlorella* suspension; and (4) storing the *Chlorella* suspension at −20° C. for 24 hours, and then thawing the frozen *Chlorella* suspension to 40° C. to 50° C. within 10 minutes by microwaves or infrared rays, so that the *Chlorella* cells are unable to reproduce. The *Chlorella* suspension is diluted with sterile water to appropriate concentration to obtain the fresh *Chlorella* drink and rapidly freeze the fresh *Chlorella* drink at −20° C. for storage. (After 4 years of clinical experiments, the results show that in the non-frozen state, the functional effect of *Chlorella* will gradually reduce to disappear.)

COMPARATIVE EXAMPLE 1

Preparation of the Conventional *Chlorella* Products

Figure 3:
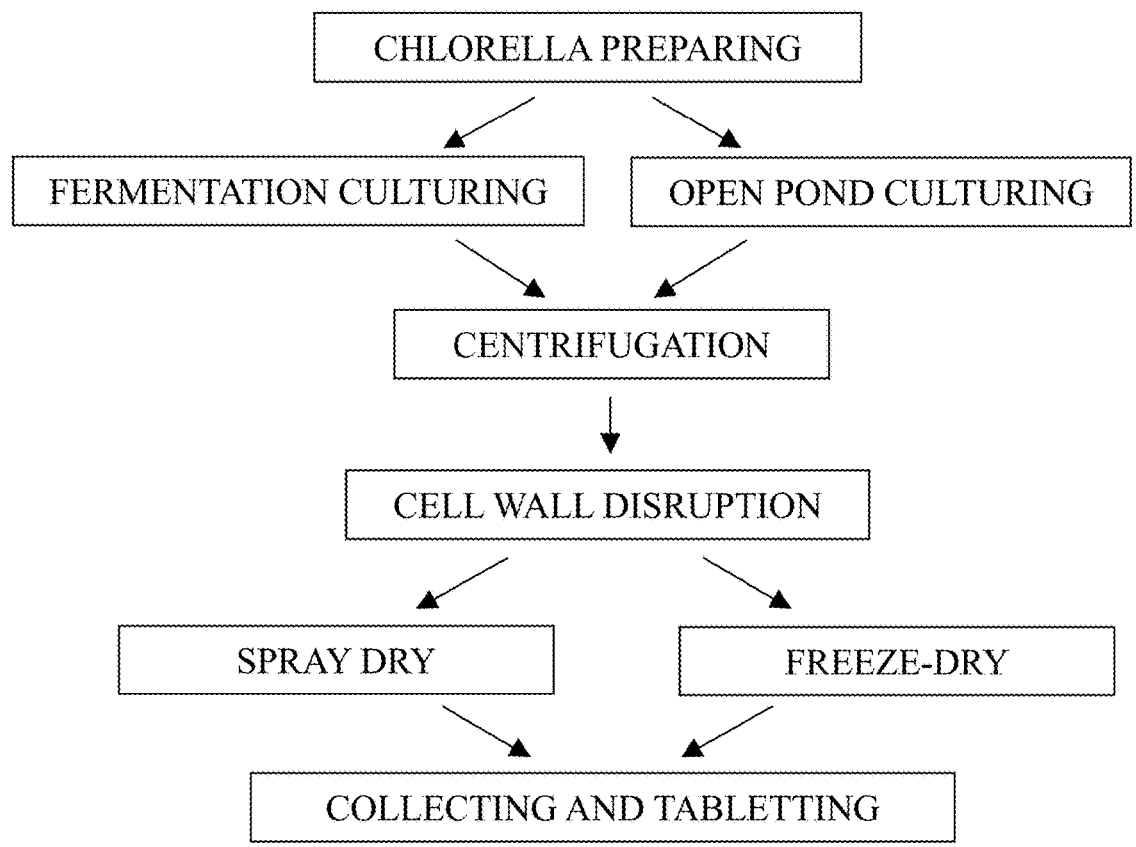
FIG. 3 is a flow chart of the conventional method for preparing a *Chlorella* product.

Referring to FIG. 3, the conventional method for preparing the conventional *Chlorella* products is fermentation culture and the open pond culture of the *Chlorella* to form a conventional *Chlorella* solution, wherein the carbon source for fermentation culture is glucose, the stirring speed ranges from 50 rpm to 100 rpm, and culturing period ranges from 5 days to 10 days. Thus, the *Chlorella* cells obtained from fermentation culture are totally not the planktonic algae but the *Chlorella* variants which will precipitate and die once the stirring stops. The carbon source for open pond culture is acetic acid, the stirring speed is faster than 10 m/s, and the culturing period required is 2 weeks to 8 weeks. The *Chlorella* cells obtained from open pond culture are also the *Chlorella* variants that will precipitate and die once the stirring stops. Moreover, open pond culture leads to accumulation of environmental toxins and contamination of bacteria.

The conventional *Chlorella* solution obtained from fermentation culture or open pond culture then undergoes centrifugation and cell wall disruption to obtain a *Chlorella* concentrate, wherein the cell wall destruction is processed at a temperature of 115° C. to 125° C., which completely destroys the anticancer function of the *Chlorella*.

The *Chlorella* concentrate is further spray dried or freeze-dried to form *Chlorella* powder, wherein the temperature of spray drying is from 155° C. to 180° C., which completely destroys the anticancer function of the *Chlorella*.

The *Chlorella* powder is collected, and the *Chlorella* powder obtained by spray drying is referred to as group A, the *Chlorella* powder obtained by freeze drying as group B, and the fresh *Chlorella* drink prepared in Preparation example 1 as group C.

EXAMPLE 1

Anticancer Use of the Fresh *Chlorella* Drink

The *Chlorella* powders of group A and group B obtained from the comparative example 1 were both prepared to reach 10 mg/kg concentration, and the concentration of the fresh *Chlorella* drink obtained from the preparation example 1 was 10 mg/ml.

24 BALB/c mice were divided into four groups, and MDA-MB-231 breast cancer cells ($1 \times 10^6$ cells/100 μl, diluted with PBS) were injected into the mammary gland of each mouse as day 0 under the orthotopic model. When the tumor has grown to 58 mm$^3$ on day 4, the control group, the group A, the group B, and the group C were respectively mixed into the fodder and were applied every 6 hours, twice a day (1 cc/kg each time). The volumes of the tumors were respectively measured on day 15 and day 22.

Figure 2A:
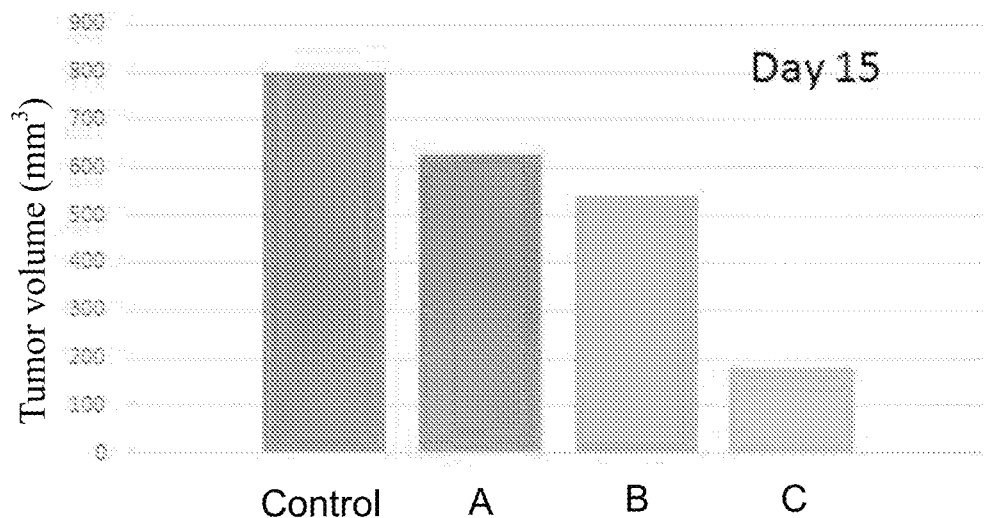
FIG. 2A is a histogram of the tumor sizes measured on the 15$^{th}$ day administered with the fresh *Chlorella* drink obtained by the method of the present invention for inhibiting cancer cells.
Figure 2B:
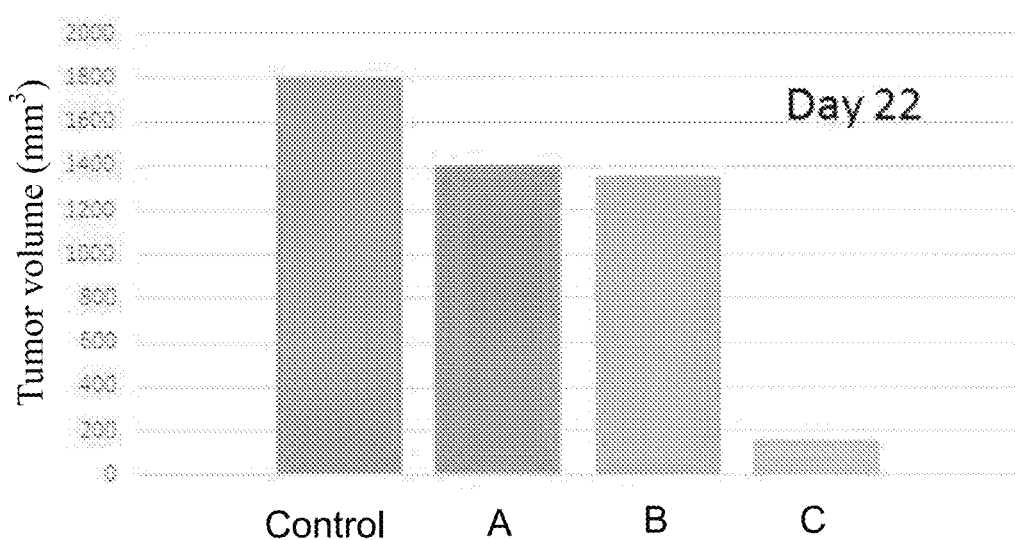
FIG. 2B is a histogram of the tumor sizes measured on the 22$^{th}$ day administered with the fresh *Chlorella* drink obtained by the method of the present invention for inhibiting cancer cells.

Referring to FIG. 2A, the growth rate of the tumor of group C was significantly slower than those of the control group, the group A, and the group B. Referring to FIG. 2B, the volume of the tumor cells of group C reduced and shrunk, while those of the control group, the group A, and the group B all increased.

EXAMPLE 2

The Measurement of *Chlorella* Growth Factor (CGF)

Content of the *Chlorella* growth factor was measured by CNS No. 4202, category No. N5134 edible green algae, the determination of 4.5 algae hot water extract value, and compared with the related products that are commercially available.

Commercially available green algae products of three brands, Brand T, Brand G, and Brand V, and the fresh *Chlorella* drink of the present invention were measured by the above determination method and the index values obtained were 1.7 (Brand T), 2.3 (Brand G), 1.6 (Brand V), and 3.8 to 4.9 (the fresh *Chlorella* drink of the present invention). Thus, these results show that content of the *Chlorella* growth factor of the fresh *Chlorella* drink obtained from the method of the present invention is more than twice as those of the commercially available green algae products.

EXAMPLE 3

The Measurement of Chlorophyll

Chlorophyll is easily degraded during improper production, processing and storage. Therefore, chlorophyll is representative of the stability of *Chlorella* quality. In this embodiment, the chlorophyll content was measured by CNS No. 4202, category No. N5134, the determination of chlorophyll in edible green algae, and compared with the related products that are commercially available. According to the CNS No. 4202, category No. N5134 regulation, the required chlorophyll content is 1500 mg % or more. After measurement, the total chlorophyll content of the related products was 2000 mg % or less, while that of the fresh *Chlorella* drink was 3800 mg % to 4900 mg %. Thus, the chlorophyll content of the fresh *Chlorella* drink obtained from the method of the present invention is more than twice as those of the commercially available green algae products.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for preparing a fresh *Chlorella* drink, comprising the steps of:
   (a) sterilely culturing and stirring *Chlorella* for not longer than 3 days, until the concentration of the *Chlorella* is over 0.05% by weight,
   (b) harvesting the culture of *Chlorella* within 6 hours;
   (c) cooling the harvested culture obtained in step (b) to lower than 1° C. but not to a frozen state, then
   (d) centrifuging the cooled culture obtained in step (c), and
   (e) adding sterile water to obtain a *Chlorella* suspension, wherein the concentration of the *Chlorella* is from 2.5 mg/ml to 12.5 mg/ml; and
   (f) freezing the *Chlorella* suspension obtained in step (e) to be completely frozen for 12 hours to 24 hours and then
   (g) increasing the temperature to 40° C. to 50° C. within 10 minutes to obtain the fresh *Chlorella* drink.

2. The method according to claim 1, wherein the stirring in step (a) is from 3 m/min to 20 m/min.

3. The method according to claim 1, wherein, in step (g), the temperature is raised by microwaves or infrared rays.

4. The method according to claim 1, wherein, in step (f), the frozen temperature ranges from −1° C. to −21° C.

5. The method according to claim 1, wherein, in step (g), the period of raising the temperature is from 3 minutes to 10 minutes.

* * * * *